United States Patent [19]
Haruta et al.

[11] Patent Number: 6,124,505
[45] Date of Patent: Sep. 26, 2000

[54] PROCESS FOR THE PARTIAL OXIDATION OF HYDROCARBON AND PROCESS FOR PREPARATION OF OXYGEN-CONTAINING ORGANIC COMPOUND

[75] Inventors: Masatake Haruta; Yuri Angelov Kalvachev; Susumu Tsubota, all of Ikeda; Toshio Hayashi, Kobe; Masahiro Wada, Nishinomiya, all of Japan

[73] Assignees: Agency of Industrial Science and Technology, Tokyo; Nippon Shokubai Co., Ltd., Osaka, both of Japan

[21] Appl. No.: 09/181,917

[22] Filed: Oct. 29, 1998

[30] Foreign Application Priority Data

Nov. 5, 1997 [JP] Japan ..................... 9-302833

[51] Int. Cl.$^7$ .................................. C07C 45/33
[52] U.S. Cl. ............... 568/360; 568/401; 568/910.5; 549/523; 549/533; 502/243
[58] Field of Search ................... 549/523, 533; 568/360, 401, 470, 475, 910.5; 502/243, 309, 350

[56] References Cited

U.S. PATENT DOCUMENTS 5,623,090  4/1997  Haruta et al. ..................... 568/360

FOREIGN PATENT DOCUMENTS

| 0 709 360 A1 | 5/1996 | European Pat. Off. . |
| 0 827 779 A1 | 3/1998 | European Pat. Off. . |
| 7-008797 | 5/1995 | Japan . |
| 1 308 380 | 2/1973 | United Kingdom . |
| WO 98/00413 | 1/1998 | WIPO . |
| WO 98/00414 | 1/1998 | WIPO . |
| WO 98/00415 | 1/1998 | WIPO . |

OTHER PUBLICATIONS

Haruta, M. "Gold as low–temperature oxidation catalyst", STUD. SURF. SCI. CATAL. (Proceeding of the 3rd World Congress on Oxidation Catalysis, San Diego, CA, Sep. 21–26, 1997) vol. 110, pp. 123–134 (1997).

*Primary Examiner*—Johann Richter
*Assistant Examiner*—Sreeni Padmanabhan
*Attorney, Agent, or Firm*—Armstrong, Westerman, Hattori, McLeland & Naughton

[57] ABSTRACT

The invention provides a catalyst for partial oxidation of hydrocarbon in the presence of a reducing compound, the catalyst comprising ultra-fine gold particles immobilized on a titanium-containing oxide, and a process for preparing an oxygen-containing organic compound, the process comprising the step of oxidizing hydrocarbon with oxygen in the presence of the above catalyst and a reducing compound.

5 Claims, No Drawings

PROCESS FOR THE PARTIAL OXIDATION OF HYDROCARBON AND PROCESS FOR PREPARATION OF OXYGEN-CONTAINING ORGANIC COMPOUND

FIELD OF THE INVENTION

The present invention relates to a catalyst for partial oxidation of hydrocarbon and a process for preparing an oxygen-containing organic compound using the catalyst.

PRIOR ART

A process for converting hydrocarbon into an oxygen-containing compound using oxygen is very useful and has given various benefits to the modern chemical industry. However, it is considered difficult, with some exceptions, to produce an alcohol and a ketone as useful compounds directly from saturated hydrocarbon or to produce an expoxide directly from unsaturated hydrocarbon. For example, only the production of cyclohexanol or cyclohexanone from cyclohexane is industrially carried out in the technique of converting saturated hydrocarbon into an alcohol and a ketone using molecular oxygen as an oxidizing agent. While the production of ethylene oxide from ethylene is industrially conducted in the techniques of converting unsaturated hydrocarbon into an epoxide, it is thought that great difficulty is encountered in a one-step preparation of an epoxide from other unsaturated hydrocarbon, e.g. propylene oxide from propylene.

Some conventional techniques are described in publications concerning the conversion of saturated hydrocarbon into an alcohol and a ketone and the conversion of unsaturated hydrocarbon into an epoxide by oxidation reaction using molecular oxygen. However, these techniques pose problems that a reaction temperature of 200° C. or higher is required and that even if the product of partial oxidation is obtained at an intermediate stage, said product is further successively oxidized. That is, the techniques are thought unsuitable for practical use.

Japanese Unexamined Patent Publication No.127550/1996 discloses a process for preparing an oxygen-containing organic compound such as an alcohol, a ketone, an epoxide or the like by oxidation of hydrocarbon with oxygen using a gold-titanium oxide-containing catalyst in the presence of molecular hydrogen. The disclosed process, however, has the following drawback. The oxidation temperature is limited to about 50 to about 150° C. at which the oxidation of hydrogen proceeds at a proper rate. If the reaction is effected at a higher temperature, the oxidation of hydrogen excessively proceeds, disadvantageously leading to a reduced conversion of hydrocarbon to oxygen-containing organic compound. To avoid this disadvantage, the oxidation temperature is limited. Consequently, the process is applicable only to limited hydrocarbons among those of various reactivities. For example, in preparation of an oxygen-containing organic compound having a high boiling point, the reaction product is not desorbed from the surface of the catalyst due to too low a reaction temperature and is further oxidized to give carbon dioxide, resulting in lower selectivity.

DISCLOSURE OF THE INVENTION

The present invention was accomplished to overcome the foregoing problems. A primary object of the invention is to provide a process for preparing an oxygen-containing organic compound from hydrocarbon, the process being capable of stably producing the compound at a high selectivity and a high conversion, and the process being widely applicable to hydrocarbons of different reactivities.

In view of the foregoing prior art problems, the present inventors conducted extensive research and found the following. When hydrocarbon is partially oxidized with molecular oxygen using a catalyst comprising ultra-fine gold particles immobilized on a titanium-containing oxide in the presence of a reducing compound such as carbon monoxide, nitrogen monoxide or the like, the desired oxygen-containing organic compound can be stably obtained in a wider temperature range and at a higher selectivity and a higher conversion than when a reaction is conducted in the presence of molecular hydrogen. The present invention was completed based on this novel finding.

According to the present invention, there are provided the following catalysts for partial oxidation of hydrocarbon and the following processes for preparing an oxygen-containing organic compound:

1. a catalyst for partial oxidation of hydrocarbon in the presence of a reducing compound, the catalyst comprising ultra-fine gold particles immobilized on a titanium-containing oxide;

2. the catalyst as defined in item 1, wherein the ultra-fine gold particles have a particle size of 10 nm or less;

3. the catalyst as defined in item 1 or 2, wherein the titanium-containing oxide is at least one oxide selected from the group consisting of titanium oxide, titanium-containing complex oxide and titanium-containing silicate;

4. a process for preparing an oxygen-containing organic compound, the process comprising the step of oxidizing hydrocarbon with oxygen in the presence of the catalyst as defined in any one of items 1–3 and a reducing compound;

5. the process as defined in item 4, wherein the reducing compound is at least one compound selected from the group consisting of carbon monoxide, nitrogen monoxide, dinitrogen monoxide, alcohols, aldehydes, phenols, formic acids, oxalic acids and cyclohexadienes;

6. the process as defined in item 4 or 5, wherein an alcohol and/or a ketone is produced by partial oxidation of saturated hydrocarbon; and 7. the process as defined in item 4 or 5, wherein an epoxide is produced by partial oxidation of unsaturated hydrocarbon.

The catalyst for partial oxidation of hydrocarbon according to the present invention (hereinafter referred to merely as "catalyst") comprises ultra-fine gold particles immobilized on a titanium-containing oxide.

Preferably the gold in the catalyst of the present invention is in the form of ultra-fine particles having a particle size of 10 nm (nanometer) or less, and the ultra-fine gold particles are supported as firmly immobilized on a titanium-containing oxide as a support.

The proportion of the gold in the catalyst of the present invention is preferably at least 0.001% by weight, more preferably 0.01 to 20% by weight, most preferably 0.05 to 10% by weight, based on the titanium-containing oxide. If the proportion of the gold supported on the oxide is less than 0.001% by weight, the activity of the catalyst is reduced. Hence it is undesirable. On the other hand, even if the proportion of the gold supported on the oxide is more than 20% by weight, the catalytic activity is not further improved over that of the gold supported on the oxide in the above proportion range. Thus the surfeit of gold is of no use. Hence the proportion outside said range is undesirable.

The type of the titanium-containing oxide is not limited. For example, titanium oxide, titanium-containing complex oxide, titanium-containing silicate or the like can be used. Especially suitable are those having a great specific surface area. The shape of the titanium-containing oxide is not limited, and includes, for example, powders and other shapes of moldings.

The titanium-containing oxides can be used alone or in combination.

Among these titanium-containing oxides, preferred titanium oxides are those having relatively small primary particle size of about 10 to about 200 nm and having a relatively large specific surface area of about 5 m$^2$/g or more.

Preferred examples of the titanium-containing complex oxide are those having a relatively large specific surface area such as titania-silica, titania-alumina, titania-zirconia and the like. Other preferred examples thereof include oxides such as $FeTiO_3$, $CaTiO_3$, $SrTiO_3$, etc. Among them, it is suitable to use complex oxides wherein titanium oxide is supported as highly dispersed on an oxide carrier having a large specific surface area.

Favorable titanium-containing silicates are porous materials containing titanium in the silica network. More preferred titanium-containing silicates are those having a large specific surface area and containing titanium atoms (Ti$^{4+}$) as highly dispersed and isolated in the network of silica. Such titanium-containing silicates are known. For example, it is desirable to use zeolite (X type, Y type, ZSM-5, ZSM-48, etc.) materials wherein aluminum is partly replaced with titanium, and titanium is incorporated in the zeolite lattice, materials wherein mesoporous silica having large mosopores (MCM-41, MCM-48, MCM-50, etc.) is partly replaced with titanium atoms, microporous titanosilicalite (so-called TS-1, Ts-2, etc.) which is a titanium-silicon complex oxide, and so on. Useful titanium-containing silicates include those wherein a small amount of titanium oxide is supported as highly dispersed on these titanium-containing silicates.

The proportion of the titanium in the titanium-containing silicate is in the range of preferably 1/1000 to 20/100, more preferably 1/100 to 10/100, calculated as the Ti—Si atom ratio (hereinafter referred to as "Ti/Si"). If the proportion of the titanium is less than Ti/Si=1/1000, the catalyst exhibits the same degree of catalytic performance as a catalyst comprising silica support alone, and selective oxidation of hydrocarbon does not occur. Hence the proportion of the titanium outside said range is undesirable.

The titanium-containing oxide can be used as immobilized on a molded carrier to further increase the catalytic activity. Useful carriers are titanium-free metallic oxides, materials produced from various kinds of metals, or the like. Examples are ceramics made from alumina (aluminum oxide: $Al_2O_3$), silica (silicon dioxide: $SiO_2$), magnesia (magnesium oxide: MgO), cordierite, zirconium oxide, complex oxides thereof or the like, foamed products made from metals, honeycomb carriers made from metals, pellets of metals, etc.

Preferred carriers are those containing at least one of alumina and silica. Among them, those containing silica are more preferred. The term "those containing . . . alumina and silica" is used herein to include carriers containing zeolite (aluminosilicate) or silica alumina.

There is no restriction on the foregoing carriers with respect to the crystal structure, shape, size and the like. However, preferred are carriers having a specific surface area of preferably 50 m$^2$/g or more, more preferably 100 m$^2$/g or more. At 50 m$^2$/g or more, side reactions such as successive oxidation can be more inhibited, resulting in efficient partial oxidation of hydrocarbon and in increase of catalytic activity.

When the titanium-containing oxide is used as immobilized on a carrier, a preferable amount of the titanium-containing oxide to be used is about 1 to about 20% by weight based on the carrier. The titanium-containing oxide can be supported on silica, alumina or like carriers by a zol-gel method using alkoxide, a kneading method, a coating method or the like. According to these methods, the titanium-containing oxide can be immobilized as dispersed on the carrier to provide the so-called island structure.

Next, a process for preparing the catalyst for use in the invention is described.

The process for preparing the catalyst to be used in the invention can be any process insofar as it is capable of immobilizing ultra-fine gold particles on a titanium-containing oxide.

Specific examples of such process include a precipitation processes, e.g. the process of producing a titanium-containing metallic oxide having ultra-fine gold particles immobilized thereon which process is disclosed in Japanese Unexamined Patent Publication No.8797/1995. The processes are briefly described below.

(I) First process

An aqueous solution containing a titanium-containing oxide is adjusted to a pH of 7–11, preferably 7.5–10. An aqueous solution containing a gold compound is added dropwise with stirring to the aqueous solution containing the titanium-containing oxide to precipitate gold hydroxide on the titanium-containing oxide. Then the titanium-containing oxide with the precipitate of gold hydroxide is heated to a temperature of 100 to 800° C. to deposit and immobilize the ultra-fine gold particles on the titanium-containing oxide.

The amount of the titanium-containing oxide to be added to water is not limited. For example, a powdery titanium-containing oxide can be used in such an amount that the oxide is uniformly dispersed or suspended in water, suitably in an amount of about 10 to about 200 g/l. When the titanium-containing oxide is used in the form of a molded product, the amount of the oxide used is not limited insofar as the aqueous solution can sufficiently contact the surface of molded products having variable shapes.

Examples of the gold compound to be used in the form of an aqueous solution are chloroauric acid ($HAuCl_4$), sodium chloroaurate ($NaAuCl_4$), gold cyanide (AuCN), potassium cyanoaurate $\{K[Au(CN)_2]\}$, trichlorodiethylamineauric acid $[(C_2H_5)_2NH \cdot AuCl_3]$ and like water-soluble gold salts. There is no limitation on the concentration of the gold compound in the aqueous solution to be added dropwise. A suitable concentration is in the range of about 0.1 to about 0.001 mol/l.

An alkali compound is usually used to adjust a solution containing the titanium-containing oxide to the specified pH range. Examples of the alkali compound to be used are sodium carbonate, sodium hydroxide, potassium carbonate, ammonia and the like.

The aqueous solution of the gold compound needs to be gradually added dropwise with stirring to the solution containing the titanium-containing oxide to prevent excessive precipitation of gold hydroxide due to abrupt reaction. Usually the time period of dropwise addition is determinable over the range of about 3 to about 60 minutes depending on the amount of the aqueous solution to be added dropwise. And the rate of dropwise addition is suitably adjusted so as to avert the excessive precipitation of gold hydroxide in the liquid phase.

The temperature of the solution containing the titanium-containing oxide in dropwise addition is suitably in the range of about 20 to about 80° C.

The amount of the aqueous solution of the gold compound to be added dropwise is determinable according to the amount of ultra-fine gold particles to be supported on the titanium-containing oxide.

When the titanium-containing oxide having the gold hydroxide precipitated thereon is heated to 100 to 800° C., the gold hydroxide is decomposed, whereby gold is uniformly deposited as ultra-fine particles on the titanium-containing oxide and is firmly immobilized thereon. The heating time is usually about 1 to about 24 hours.

(II) Second process

An aqueous solution of a reducing agent is added dropwise with stirring to an aqueous solution containing a gold compound and a titanium-containing oxide with a pH of 7 to 11 (preferably 7.5 to 10) to deposit ultra-fine gold particles due to reduction on the surface of the titanium-containing oxide and to immobilize them on its surface.

As to the gold compound, the titanium-containing oxide and the pH-adjusting alkali compound, the same species exemplified above for the first process may be used in the second process. The amount of the titanium-containing oxide to be used in the second process may be the same as in the first process. A suitable concentration of the gold compound in the solution to be used in the second process is about $1 \times 10^{-2}$ to about $1 \times 10^{-5}$ mol/l. A proper reaction temperature of the aqueous solution containing the titanium-containing oxide is about 0 to about 80° C.

Examples of useful reducing agents are hydrazine, formalin, sodium citrate and the like. The concentration of the reducing agent in the solution is about $1 \times 10^{-1}$ to about $1 \times 10^{-3}$ mol/l. A suitable amount of the aqueous solution of the reducing agent to be used is about 1.5 to about 10 times the stoichiometric amount. The aqueous solution of the reducing agent needs to be gradually added dropwise to avert abrupt deposition of gold from the reaction mixture. The dropwise addition is usually carried out over a period of about 3 to about 60 minutes.

The obtained titanium-containing oxide having ultra-fine gold particles immobilized thereon can be used as such at room temperature. However, when used at a high temperature, the titanium-containing oxide having ultra-fine gold particles immobilized thereon is desirably heated to almost the same temperature as the reaction temperature before use in order to improve the stability of the catalyst at a high temperature.

(III) Third process

A carbon dioxide gas is blown into an aqueous solution containing a gold compound and a titanium-containing oxide with a pH of at least 11 (preferably 11 to 12), or an acidic aqueous solution is gradually added dropwise with stirring to the aqueous solution to decrease the pH to 7–11, thereby precipitating gold hydroxide on the titanium-containing oxide. Thereafter the titanium-containing oxide is heated to 100 to 800° C. to deposit ultra-fine gold particles on the surface of titanium-containing oxide.

As to the gold compound, the titanium-containing oxide and the alkali compound, the same amounts of the same species as used in the first process may be used in the third process. Suitably the aqueous solution containing the titanium-containing oxide is used in the reaction at a temperature of about 20 to about 80° C.

In the third process, the gold compound in the aqueous solution containing the titanium-containing oxide needs to remain dissolved therein as the complex ions having hydroxyl group excessively bonded thereto. Consequently the pH of the aqueous solution containing the titanium-containing oxide is adjusted to at least 11 and controlled such that the gold compound is dissolved as hydroxyl-containing complex ions according to the gold compound to be used.

A carbon dioxide gas is blown into the aqueous solution in such state, or alternatively an acidic aqueous solution is gradually added dropwise to the aqueous solution to slowly lower the pH of the solution to 7–11, whereby gold hydroxide is precipitated on the surface of titanium-containing oxide as a core and adheres thereto.

The rate of blowing a carbon dioxide gas is not limited and is in the range wherein the reaction mixture is uniformly bubbled.

Useful acidic aqueous solutions include, for example, aqueous solutions of nitric acid, hydrochloric acid, sulfuric acid, acetic acid or the like. These acidic aqueous solutions can be used in a concentration of about $1 \times 10^{-1}$ to about $1 \times 10^{-3}$ mol/l. The amount of the solution to be added dropwise is in the range wherein the solution containing the titanium-containing oxide is not given a pH of less than 7. The time period of dropwise addition can be suitably determined over the range of about 3 to about 60 minutes according to the amount of the solution to be added so as to avoid excessive precipitation of gold hydroxide in the liquid phase.

Then, when the titanium-containing oxide having the gold hydroxide precipitated thereon is heated to 100 to 800° C., the gold hydroxide is decomposed, whereby gold is uniformly deposited as ultra-fine particles on the titanium-containing oxide and is firmly immobilized thereon. The heating time is usually about 1 to about 24 hours.

Preferably the aqueous solution containing the titanium-containing oxide is stirred for about 30 minutes to about 2 hours after completion of dropwise addition of the solution or gas blowing to precipitate the gold compound on the titanium-containing oxide to a satisfactory extent.

The catalyst for use in the invention can be also prepared according to the process for preparing a material having ultra-fine gold particles immobilized thereon using a vapor of organic gold complex which process is disclosed in Japanese Unexamined Patent Publication No.122478/1997. The disclosed process is briefly described below.

In this process, vaporized organic gold complex is adsorbed on a titanium-containing oxide under reduced pressure and heated to 100 to 700° C., giving titanium-containing oxide having ultra-fine gold particles immobilized thereon.

Useful organic gold complexes are not limited insofar as they are volatile. For example, use is made of at least one of $(CH_3)_2Au(CH_3COCHCOCH_3)$, $(CH_3)_2Au(CF_3COCHCOCH_3)$, $(CH_3)_2Au(CF_3COCHCOCF_3)$, $(C_2H_5)_2Au(CH_3COCHCOCH_3)$, $(CH_3)_2Au(C_6H_5OOCHCOCF_3)$, $CH_3C_2AuP(CH_3)_3$, and $CH_3AuP(CH_3)_3$.

Before use, the titanium-containing oxide may be heat-treated at about 200° C. to remove water or the like from its surface.

The organic gold complex can be vaporized by heating. The heating temperature is not limited insofar as it is in the range which will not cause abrupt vaporization and adsorption, or decomposition. The range is usually about 0 to about 90° C. The vaporization can be effected under reduced pressure ranging from about $1 \times 10^{-4}$ to about $2 \times 10^{-3}$ Torr.

The vaporized organic gold complex is adsorbed on a titanium-containing oxide under reduced pressure. The term "under reduced pressure" used herein refers to the pressure below the atmospheric pressure and usually a pressure in the range of about $1 \times 10^{-4}$ to about 200 Torr. The amount of the organic gold complex to be used is variable depending on the type of gold complex to be used and is suitably adjusted to the amount finally corresponding to the foregoing amount of immobilized gold. The pressure may be adjusted by, e.g. a conventional vacuum pump.

Subsequently the titanium-containing oxide having the organic gold complex adsorbed thereon is heated in air to about 100 to about 700° C., preferably to about 300 to about 500° C. Thereby the organic components in the organic gold complex are decomposed and oxidized, and the organic gold is reduced to gold, which is then deposited as ultra-fine particle on the titanium-containing oxide and immobilized thereon. The heating time can be suitably determined according to the amount of the gold complex to be immobilized, heating temperature, etc. It is usually in the range of about 1 to about 24 hours. In this way, the procedure gives a titanium-containing oxide having ultra-fine gold particles immobilized thereon.

In the foregoing process, the titanium-containing oxide may be surface-treated by heating usually at about 100 to about 700° C. before adsorption of organic gold complex. The surface treatment can be effected in the atmosphere of oxidized gas or reducing gas. When the surface treatment is conducted, the amount of defective portion and the state on the surface of titanium-containing oxide are more easily controlled, thereby making it possible to more finely control the particle size and the amount of gold particles to be immobilized.

Useful oxidizing gases include conventional ones such as oxygen gas, nitrogen monoxide gas, etc. Useful reducing gases include conventional ones such as hydrogen gas, carbon monoxide gas, etc.

According to the gold-precipitating process and the organic gold complex-vaporizing process described above, ultra-fine gold particles can be firmly immobilized on the titanium-containing oxide in relatively uniform distribution.

When said catalyst is used as immobilized on the carrier, a suitable process is one comprising causing a titanium-containing oxide to become immobilized on a carrier and then immobilizing gold particles on the oxide. To immobilize the gold on the titanium-containing oxide supported on a carrier, the carrier having the titanium-containing oxide supported thereon can be used in place of the titanium-containing oxide in the gold-precipitating process and the organic gold complex-vaporizing process described above. The gold-precipitating process is advantageous in that the ultra-fine gold particles are immobilized only on the titanium-containing oxide (especially in the position of titanium ions) while being scarcely deposited on the carrier. When a carrier consisting of or containing silica is used, the gold-precipitating process is pronouncedly advantageous in that ultra-fine gold particles can be immobilized only on the titanium-containing oxide with a high selectivity.

Discussed next is a method of partial oxidation of hydrocarbon using a catalyst comprising ultra-fine gold particles immobilized on the titanium-containing oxide.

Examples of hydrocarbons useful as the raw material are saturated hydrocarbons having about 3 to about 12 carbon atoms and unsaturated hydrocarbons having about 2 to about 12 carbons. When the reaction is carried out in a gaseous phase, it is suitable to use a hydrocarbon having 6 or less carbon atoms the reaction product of which is easily desorbed from the catalyst layer even at a low temperature of about 100° C. Useful hydrocarbons are, for example, saturated hydrocarbons such as propane, n-butane, isobutane, cyclobutane, n-pentane, 2-methylbutane, cyclopentane, n-hexane, 2-methylpentane, 3-methylpentane, cyclohexane, etc. and compounds having a double bond, as unsaturated hydrocarbons, such as ethylene, propylene, 1-butene, 2-butene, isobutene, 1-pentene, 2-pentene, 2-methyl-1-butene, 3-methyl-1-butene, cyclopentene, 1-hexene, 2-hexene, 3-hexene, 2-methyl-l-pentene, 3-methyl-1-pentene, cyclohexene, 1-methyl-1-cyclopentene, 3-methyl-1-cyclopentene, 4-methyl-1-pentene, etc.

When a saturated hydrocarbon is used as the raw material, a ketone is predominantly produced by oxidation of secondary carbon-hydrogen bond, while an alcohol is predominantly produced by oxidation of tertiary carbon-hydrogen bond. In the oxidation of carbon-hydrogen bond, reactivity is higher in the order of tertiary carbon, secondary carbon and primary carbon. Substantially no reaction is induced by oxidation of primary carbon-hydrogen bond.

When an unsaturated hydrocarbon is used as the raw material, an epoxide is produced with a high selectivity.

The catalyst to be used in the process of the invention comprises ultra-fine gold particles immobilized on the titanium-containing oxide. The amount of the catalyst to be used is not limited, but practically it is suitable to use the catalyst in the amount range wherein in an gaseous-phase reaction, a space velocity (SV) is in the range of about 100 to about 10000 $hr^{-1} \cdot ml/g \cdot cat$.

In the present invention, a hydrocarbon is essentially oxidized with oxygen in the presence of a reducing compound. The contemplated oxygen-containing compound can be obtained by oxidation in the presence of a reducing compound in a wide temperature range with a high selectivity and a high conversion. Therefore even when a wide variety of hydrocarbons having different reactivities are used as the raw material, the contemplated oxygen-containing compound can be obtained at a properly selected reaction temperature with a high selectivity and a high conversion for a long term. Furthermore, the catalytic activity is scarcely diminished in the process of the invention, so that the oxygen-containing compound can be produced with a stable conversion for a long term.

On the other hand, if a reducing compound is not used, namely, if the reaction is effected in the presence of the catalyst using a mixed gas containing oxygen, hydrocarbon and optionally a diluted gas, a reaction starts to proceed at 200° C. or more, but produces mainly carbon dioxide without producing the desired product of partial oxidation at all.

When hydrogen is used in place of a reducing compound, a product of partial oxidation is produced in a limited temperature range. If a reaction is conducted in this case at too high a temperature, a combustion reaction occurs forming carbon dioxide while oxidation of hydrogen to water proceeds in an increased degree, leading to a lower conversion to the desired product of partial oxidation. Further, when hydrogen is used along with the catalyst containing a titanium oxide or a titanium-containing complex oxide, the catalytic activity is lowered with time, resulting in a decrease of conversion.

It is desirable in the present invention to use, as a reducing compound, e.g. carbon monoxide, nitrogen monoxide, dinitrogen monoxide or like reducing inorganic compounds, alcohols, aldehydes, phenols, formic acids, oxalic acids or like reducing organic compounds. These reducing compounds can be used either alone or in combination.

Among these compounds, useful alcohols can be any of primary alcohol, secondary alcohol and tertiary alcohol. Suitable examples are methanol, ethanol, 1-propanol, 2-propamol, 1-butanol, 2-butanol, 2-methyl-2-propanol and cyclohexanol. Useful aldehydes are, for example, formaldehyde, acetoaldehyde, propanal, 2-methylpropanal, acrolein, methacrolein and benzaldehyde. Useful phenols are, for example, phenol, o-, m- or p-cresol, 2,6-dimethylphenol, p-hydroquinone and o-resorcin. Useful formic acids are, for example, formic acid, methyl formate, ethyl formate and like esters of formic acid. Useful oxalic acids are, for example, oxalic acid, dimethyl oxalate, diethyl oxalate and like esters of oxalic acid. Useful cyclohexadienes include, for example, 1,3-cyclohexadiene and the like.

The amount of the reducing compound to be used in the invention is not limited. Under the reaction conditions under which the raw materials and the reducing compound are vaporized, usually a suitable volume ratio of reducing compound/raw materials is in the range of approximately from 1/10 to 100/1. Generally the larger the proportion of the reducing compound is, the higher the reaction rate is. Thus, it is desirable to select a larger proportion in said range.

The amount of oxygen to be present in the invention is not limited. Yet a suitable volume ratio of oxygen/raw materials is in the range of approximately from 1/10 to 10/1. Below the range, a product of partial oxidation is formed undesirably in a reduced amount. On the other hand, above said range, a product of partial oxidation is produced at a lower selectivity (increased amount of carbon dioxide produced) without increasing the amount of the product. Hence it is undesirable.

The reaction temperature in the invention is suitably in the range of about 30 to about 300° C., preferably about 80 to about 250° C. According to the invention, a product of partial oxidation can be obtained in such wide temperature range at a high conversion and a high selectivity due to the presence of the reducing compound. A suitable reaction temperature can be determined according to the reactivity of the hydrocarbon used as the raw material.

When the oxidation reaction of the invention is carried out in a gaseous phase, a reactor provided with the catalyst of the invention is charged with a mixed gas containing a hydrocarbon, a reducing compound, oxygen and optionally a diluted gas (such as nitrogen, argon, helium, carbon dioxide and the like). Then the reaction is conducted under the specified conditions. The mixed gas to be supplied may contain hydrogen. In the oxidation reaction of the invention in a gaseous phase, a reducing compound is used which is vaporized under the specified reaction conditions. It is desirable to select a temperature at which a reaction product exhibits the desired volatility under the specified reaction pressure (usually about 0.01 to about 1 MPa) to facilitate the desorption of reaction product from the catalyst layer.

When the reaction of the invention is conducted in a liquid phase, a reaction temperature of 100° C. or less can be employed in most cases because of non-necessity of removing the reaction product from the catalyst layer. In the liquid phase reaction, a reaction pressure and a reaction temperature are selected from the ranges in which the raw materials can be held liquid, or the reaction is performed by bubbling a mixed gas of the raw material, a reducing compound, oxygen and optionally a diluted gas in the presence of the catalyst suspended in a solvent (such as benzene and like hydrocarbon solvents, methylene chloride and like halogenated hydrocarbon solvents). The mixed gas to be supplied may contain hydrogen.

The catalyst to be used in the invention shows a high activity and a high selectivity for partial oxidation of hydrocarbon with oxygen in the presence of a reducing compound due to the synergistic effect of the gold and titanium-containing oxide in the catalyst.

The desired oxygen-containing organic compound can be stably obtained in a wide temperature range at a high selectivity and a high conversion by the partial oxidation of hydrocarbon using the catalyst of the invention in the presence of a reducing compound and oxygen. With these advantages, the desired oxygen-containing organic compound can be produced even from a wide variety of hydrocarbons of different reactivities at a properly selected reaction temperature with a high selectivity and a high conversion. This means that oxygen-containing organic compounds such as alcohols, ketones, epoxides and the like can be produced from a variety of hydrocarbons by a one-step procedure with a high selectivity and a stable conversion.

EXAMPLES

The present invention will be described below in more detail with reference to the following examples.

EXAMPLE 1

(Partial oxidation of propylene)

Dissolved in 1200 ml of distilled water was 1.0 g (2.43 mmols) of chloroauric acid·4 hydrates ($HAuCl·4 H_2O$). The solution was heated to 70° C. and adjusted to a pH of 7.5 with a 0.1N aqueous solution of NaOH. Titanium-containing silicate (6 g) was added at one time with vigorous stirring. The mixture was stirred for 1 hour at the same temperature, inducing precipitation of gold hydroxide ($Au(OH)_3$) on the titanium-containing silicate. Used as the titanium-containing silicate was a material wherein mesoporous silica is partly replaced by titanium atoms (Ti-MCM-41) (Ti/Si (atom ratio)=3/100). The suspension was left to stand and cooled to room temperature. Then the supernatant was removed, 3000 ml of distilled water was added, the mixture was stirred at room temperature for 5 minutes, and the supernatant was removed after standing. The above washing operation was repeated several times, followed by filtration. Subsequently the obtained paste was vacuum-dried at room temperature for 12 hours and was fired in air at 400° C. for 4 hours, giving a catalyst comprising ultra-fine gold particles immobilized on the titanium-containing silicate. The amount of the chloroauric acid used was 8% by weight based on the titanium-containing silicate (Ti-MCM-41). However, analysis showed that the amount of the gold immobilized on the titanium-containing silicate was 1.2% by weight.

Partial oxidation of propylene was conducted with the thus obtained catalyst using a fixed-bed flow-system catalytic reactor. Used as the reaction gas were a mixed gas of argon/$O_2$/propylene at a volume ratio of 70/10/10 and a mixed gas of argon/$O_2$/CO/propylene at a volume ratio of 70/10/10/10.

The reaction conditions were as follows.

Catalytic reaction cell: one made of quartz, 6 mm in inside diameter

Amount of catalyst: 0.5 g

Pre-treatment of catalyst: A mixed gas (argon/$O_2$ in 7/1 proportion) was passed at 300° C. for 1 hour.

Space velocity: 4000 $h^{-1}$·ml/g·cat

Reaction temperature: 100° C.

Table 1 below shows the propylene conversion in percentage, CO conversion in percentage, acrolein selectivity and propylene oxide selectivity which were determined 1 hour after the initiation of the reaction.

TABLE 1

| Composition of reaction gas | Propylene conversion (%) | CO conversion (%) | Acrolein selectivity (%) | Propylene oxide selectivity (%) | Remarks |
|---|---|---|---|---|---|
| Ar/O$_2$/propylene 70/10/10 | 0.06 | — | 81 | 0 | CO$_2$ mainly produced among other products |
| Ar/O$_2$/CO/propylene 70/10/10/10 | 0.39 | 22 | 8.3 | 27 | CO$_2$ mainly produced among other products |

The results of Table 1 reveal the following. When the catalyst comprising gold immobilized on the titanium-containing silicate was used, the presence of carbon monoxide contributed to the production of propylene oxide by partial oxidation of propylene and increased the conversion of propylene.

EXAMPLE 2

Using a catalyst produced in the same manner as in Example 1, partial oxidation of propylene was conducted by a fixed-bed flow-system catalytic reactor. Used as the reaction gas was a mixed gas of argon/O$_2$/NO/propylene at a volume ratio of 7/1/0.5/1.

The reaction conditions were as follows.
Catalytic reaction cell: one made of quartz, 6 mm in inside diameter
Amount of catalyst: 0.5 g
Pre-treatment of catalyst: A mixed gas (argon/O$_2$ in 7/1 proportion) was passed at 300° C. for 1 hour.
Space velocity: 4000 h$^{-1}$·ml/g·cat
Reaction temperature: 100° C., 120° C. and 150° C.

Table 2 below shows the propylene conversion in percentage, NO conversion in percentage, propylene oxide selectivity and propylene oxide yield which were determined 1 hour after the initiation of the reaction.

TABLE 2

| Reaction temperature (° C.) | Propylene conversion (%) | NO conversion (%) | Propylene oxide selectivity (%) | Propylene oxide yield (%) |
|---|---|---|---|---|
| 100 | 2.0 | 16 | 14 | 0.29 |
| 120 | 2.8 | 19 | 23 | 0.65 |
| 150 | 8.0 | 29 | 34 | 2.7 |

The results of Table 2 show the following. When the catalyst comprising gold immobilized on the titanium-containing silicate was used, the presence of nitrogen monoxide contributed to the control of reaction at a relatively high temperature and increased the yield of propylene oxide.

EXAMPLE 3

Used as the titanium-containing oxide was titania-silica (silica carrier manufactured by Fuji Silysia Chemical Ltd., 1% by weight of TiO$_2$ immobilized on Cariact Q-10). A catalyst comprising ultra-fine gold particles immobilized on the titanium-containing oxide was produced by the same precipitation method as in Example 1. Analysis showed that the amount of gold immobilized on the oxide was 0.2% by weight.

Using this catalyst, partial oxidation of propylene was conducted using a fixed-bed flow-system catalytic reactor. Used as the reaction gas was a mixed gas of propylene/O$_2$/argon/2-propanol at a volume ratio of 9.7/9.7/68.1/12.5.

The reaction conditions were as follows.
Catalytic reaction cell: one made of quartz, 8 mm in inside diameter
Amount of catalyst: 1 g
Pre-treatment of catalyst: A mixed gas (argon/O$_2$ in 7/1 proportion) was passed at 300° C. for 30 minutes.
Space velocity: 4000 h$^{-1}$·ml/g·cat
Reaction temperature: 160° C. and 200° C.

Table 3 below shows the propylene conversion in percentage, yield of propylene oxide and conversion in percentage of 2-propanol to acetone which were determined 1 hour after the initiation of the reaction.

TABLE 3

| Reaction temp. (° C.) | Propylene conversion (%) | Propylene oxide yield (%) | Conversion of 2-propanol to acetone (%) |
|---|---|---|---|
| 160 | 0.15 | 0.13 | 40.2 |
| 200 | 0.28 | 0.21 | 68.4 |

COMPARATIVE EXAMPLE 1

The partial oxidation of propylene was conducted in the same manner as in Example 3 with the exception of using, as the reaction gas, a mixed gas of propylene/O$_2$/argon/2-propanol at a volume ratio of 11.1/11.1/77.8/0.

Table 4 below shows the propylene conversion in percentage and yield of propylene oxide which were determined 1 hour after the initiation of the reaction.

TABLE 4

| Reaction temperature (° C.) | Propylene conversion (%) | Propylene oxide yield (%) |
|---|---|---|
| 160 | 0.1 | 0.0 |
| 200 | 0.4 | 0.0 |

EXAMPLE 4

The partial oxidation of propylene was conducted in the same manner as in Example 3 with the exception of using a mixed gas of propylene/O$_2$/argon/methanol at a volume ratio of 5.4/5.4/75.6/13.6.

Table 4 below shows the propylene conversion in percentage, yield of propylene oxide and conversion in percentage of methanol to formaldehyde and CO$_x$ which were determined 1 hour after the initiation of the reaction.

TABLE 5

| Propylene conversion (%) | Propylene oxide yield (%) | Conversion of methanol to formaldehyde and CO$_x$ (%) |
|---|---|---|
| 0.24 | 0.16 | 18.5 |

What is claimed is:
1. A process for preparing an oxygen-containing organic compound, the process comprising the steps of oxidizing hydrocarbon with oxygen in the presence of a catalyst comprising ultra-fine gold particles immobilized on a titanium-containing oxide and at least one reducing compound selected from the group consisting of carbon monoxide, nitrogen monoxide, dinitrogen monoxide, alcohols, aldehydes, phenols, formic acid, esters of formic acid, oxalic acid, esters of oxalic, and cyclohexadienes.

2. A process according to claim 1, wherein the ultra-fine gold particles have a particle size of 10 nm or less.

3. A process according to claim 1, wherein the titanium-containing oxide is at least one oxide selected from the group consisting of titanium oxide, titanium-containing complex oxide and titanium containing silicate.

4. The process according to claim 1, wherein an alcohol and/or a ketone is produced by partial oxidation of saturated hydrocarbon.

5. The process according to claim 1, wherein an epoxide is produced by partial oxidation of unsaturated hydrocarbon.

* * * * *

UNITED STATES PATENT AND TRADEMARK OFFICE
CERTIFICATE OF CORRECTION

PATENT NO.: 6,124,505
DATED : September 26, 2000
INVENTOR(S): HARUTA et al.

It is certified that an error appears in the above-identified patent and that said Letters Patent is hereby corrected as shown below:

On the title page of the patent in item [73] change the name of the first assignee, "Agency of Industrial Science & Technology" to be --Director-General, Agency of Industrial Science & Technology--

Signed and Sealed this

Fifteenth Day of May, 2001

Attest:

NICHOLAS P. GODICI

Attesting Officer

Acting Director of the United States Patent and Trademark Office